United States Patent
Hecker et al.

(10) Patent No.: US 7,504,015 B2
(45) Date of Patent: Mar. 17, 2009

(54) METHOD AND DEVICE FOR PRODUCING OXYGEN

(75) Inventors: Karl-Heinz Hecker, Hoehenbergstrasse 57, 83229 Aschau/Chiemgau (DE); Stefan Fiedler, Attenkirchen (DE); Rudolf Schinagl, Unterhaching (DE)

(73) Assignee: Karl-Heinz Hecker, Aschau/Chiemgau (DE)

( * ) Notice: Subject to any disclaimer, the term of this patent is extended or adjusted under 35 U.S.C. 154(b) by 676 days.

(21) Appl. No.: 10/472,053

(22) PCT Filed: Mar. 12, 2002
(Under 37 CFR 1.47)

(86) PCT No.: PCT/EP02/02709

§ 371 (c)(1),
(2), (4) Date: Mar. 24, 2004

(87) PCT Pub. No.: WO02/072919

PCT Pub. Date: Sep. 19, 2002

(65) Prior Publication Data
US 2004/0146759 A1    Jul. 29, 2004

(30) Foreign Application Priority Data

Mar. 12, 2001  (DE) .................................. 101 11 749
Mar. 12, 2001  (DE) ............................. 201 04 256 U
Mar. 19, 2001  (DE) ............................. 201 04 713 U

(51) Int. Cl.
C25B 1/04    (2006.01)

(52) U.S. Cl. .................... 205/343; 205/346; 205/628; 204/263; 204/266; 204/271; 204/275.1; 204/278; 429/12; 429/17; 429/19

(58) Field of Classification Search ................. 205/343, 205/628; 204/263, 266, 278, 271, 275.1; 429/12, 17, 19
See application file for complete search history.

(56) References Cited

U.S. PATENT DOCUMENTS

| 3,992,271 A | 11/1976 | Danzig et al. |
| 5,495,848 A | 3/1996 | Aylsworth et al. |

(Continued)

FOREIGN PATENT DOCUMENTS

DE          21 26 403          12/1971

(Continued)

*Primary Examiner*—Bruce F Bell
(74) *Attorney, Agent, or Firm*—Jordan and Hamburg LLP

(57) ABSTRACT

The invention relates to a method and a device for producing elementary oxygen or for increasing the concentration thereof in the inhaled air of a user. According to the invention, water is split into hydrogen and elementary oxygen by means of electrical energy (electrolysis), the elementary oxygen is mixed with the inhaled air, and the hydrogen is mixed with the surrounding air in order to be converted back into water (fuel reaction). The splitting of the water into hydrogen and elementary oxygen and the conversion of the hydrogen and surrounding air into water take place simultaneously and continuously, forming a reaction circuit, and are coupled to each other, the electrical energy produced during the conversion being used to reduce the energy demand for the splitting. To this end, an electrolyzer outfit for splitting water into hydrogen and elementary oxygen, and a fuel cell for converting the hydrogen and the surrounding air into water are electrically connected in such a way that they can conduct liquids.

32 Claims, 2 Drawing Sheets

U.S. PATENT DOCUMENTS

| | | | | |
|---|---|---|---|---|
| 5,750,077 | A * | 5/1998 | Schoen | 422/122 |
| 6,495,025 | B2 * | 12/2002 | Velev | 205/633 |
| 2002/0017463 | A1 * | 2/2002 | Merida-Donis | 204/551 |

FOREIGN PATENT DOCUMENTS

| DE | 59-162106 | 9/1984 |
|---|---|---|
| DE | 33 39 934 | 5/1985 |
| DE | 195 33 097 | 3/1997 |
| DE | 196 39 068 | 3/1998 |
| DE | 197 07 097 | 9/1998 |
| DE | 201 04 713 | 5/2001 |
| DE | 201 04 256 | 6/2001 |
| JP | 58-206070 | 12/1983 |
| JP | 62-202805 | 9/1987 |
| JP | 04-371592 | 12/1992 |
| JP | 6-260201 | 9/1994 |
| JP | 2000-54176 | 2/2000 |
| JP | 2001-333983 | 12/2001 |
| WO | WO-99/56334 | 11/1999 |

* cited by examiner

METHOD AND DEVICE FOR PRODUCING OXYGEN

BACKGROUND OF THE INVENTION

The present invention relates to a method and to a device for producing oxygen, as well as to its use in different areas.

Almost pure oxygen is frequently required when a user or a patient is to be supplied, for medical or other reasons, with correspondingly pure oxygen instead of the conventional oxygen occurring in the surrounding air.

For this purpose, essentially three possible devices and methods are known from the state of the art.

For example, so-called oxygen- or $O_2$-concentrators are used. In these, two molecular sieves are selected alternately in that air is aspirated over an air filter, compressed with a compressor and alternately supplied to the molecular sieves over valves. The molecular sieves are filled with zeolites, which absorb gases. By the pressure produced, the absorption ratio of oxygen to nitrogen is shifted in a high degree towards nitrogen, so that almost pure oxygen leaves the molecular sieve, approximately a third of which is supplied to the user or patient. In general, oxygen concentrators are defect-ridden and susceptible to failure. Moreover, the compressors are correspondingly noise-intensive and the devices are bulky.

A further possibility for producing almost pure oxygen is based on the fact that oxygen, present in the liquid state and kept in appropriate pressure vessels, is converted to the gaseous state by conversion processes adequately known from the state-of-the-art and then supplied to a patient. This possibility has the disadvantage that liquid oxygen must always be available and is associated with a certain expense, especially outside of a hospital.

Furthermore, it is also known that the oxygen required can be made available in pressure vessels. Here also, a certain logistic expenditure cannot be avoided. Moreover, the pressure vessels, which must withstand a pressure up to 200 bar, are correspondingly heavy and difficult to transport.

It is a common, significant disadvantage of the three methods and devices named above for producing oxygen that, because of their specific, structural configuration on the one hand and because they require starting materials to be made available, they are suitable only to a limited extent, if at all, for mobile use.

Starting out from the disadvantages, known from the state of the art, it is an object of the present invention to make available a method, which can make almost pure oxygen available to a user in a very simple matter. Moreover, it is an object of this invention to make available a device, which implements this method, can be handled easily, makes relatively little noise and is light.

BRIEF SUMMARY OF THE INVENTION

Basically, the present invention makes two methods available for producing oxygen.

In the case of a first, inventive method, water is split by electrolysis, which is a known method, into hydrogen and into oxygen, which is then mixed with the respired air. The hydrogen formed can then be converted once again with air from the surroundings by means of a coupled fuel reaction into water. In this connection, it is essential, pursuant to the invention, that the electrolysis and the fuel reaction are coupled with one another in such a manner, that they form a reaction cycle and take place simultaneously and continuously. Pursuant to the invention, the electrical energy, released by the fuel reaction, is then used to reduce the energy required for the splitting.

According to a further development of this method, the water, obtained during the fuel reaction, is recycled to the splitting process.

According to an advantageous development of the method, the electrical energy, required for maintaining the reaction cycle, is generated either by the fuel reaction itself, which is coupled with the electrolysis, or by a second fuel reaction, which takes place separately from the first one, additional hydrogen, which does not originate from the electrolysis or is supplied from a separate energy source, then being supplied to the two fuel reactions.

The additional hydrogen, required for this, can be made available directly from a storage medium, especially from a metal hybride storage medium or a pressurized storage medium, the hydrogen being obtained, in accordance with one embodiment of the invention, by means of a fuel reforming process, for example, from sodium borohydride.

In a further, advantageous development of this method, the fuel may, for example, be methanol.

Pursuant to the invention, oxygen can also produced in a second method owing to the fact that the electrolysis process and the fuel reaction are interwoven with one another in such a manner, that the intermediate step of transferring the hydrogen, produced by the electrolysis, into the fuel reaction, is omitted. For this purpose and pursuant to the invention, the water is split catalytically at an anode side of a cell into hydrogen ions and oxygen ions, the hydrogen ions moving through a polymer electrolyte membrane (PEM) to a cathode side of this cell, in which they are converted catalytically with air from the surroundings into water once again. At the anode side, the oxygen ions react, emitting electrons to the oxygen, which is then admixed with the respired air.

Pursuant to the invention, the water, obtained on the cathode side during this second method, can also be recycled once again to the splitting reaction on the anode side.

For this variation of the inventive method also, the electrical energy, necessary for maintaining the reaction cycle, can be made available by an additional fuel reaction, which proceeds separately from the process, in that additional hydrogen, which optionally can be reformed from a fuel, is supplied to this additional fuel reaction.

For carrying out the method mentioned first, an electrolyzer, pursuant to the invention, is connected to a fuel cell electrically and for transferring fluids.

In this connection, it is advantageous, pursuant to the invention, if the electrolyzer and/or the fuel cell are constructed as a so-called PEM cell. For the latter, a plastic membrane, which carries out the ion transport and, in so doing, conducts only protons, is used as electrolyte. The advantage of polymer membranes over potassium hydroxide as electrolyte lies in the simplification of the system and, above all, in the higher, achievable power density. Moreover, in comparison to an alkali unit, a PEM cell is not sensitive to contamination by carbon dioxide, so that it is not necessary to use very pure reaction gases and the fuel cell can also be operated with air.

When an external voltage is supplied to the PEM electrolyzer, water is split electrolytically on the anode side directly into gaseous oxygen, electrons and $H^+$ ions according to the equation $2H_2O \rightarrow 4\ e^- + 4H^+ + O_2$. The $H^+$ ions (protons) migrate through a proton-conducting PEM membrane to the cathode and, with the electrons flowing over an external conducting circuit, form hydrogen according to the equation $4H^+ + 4\ e^- \rightarrow 2H_2$, the overall reaction being $2H_2O \rightarrow 2H_2 + O_2$. The pure oxygen is then discharged and admixed with the air respired by a patient, whereas the hydrogen is passed on to a PEM fuel cell.

The mode of functioning of the fuel cell is opposite to that of the electrolysis cell. The hydrogen, supplied to the anode of this cell, is oxidized, being broken down by the catalytic action of the electrode into protons and electrons ($2H_2 \rightarrow 4H^+ + 4\ e^-$). The hydrogen ions once again reach the cathode side through a proton-conducting PEM membrane. In the case of a closed external circuit, the electrons migrate to the cathode and carry out electrical work on the way. The oxygen (not pure), which is contained in the surrounding air and carried to the cathode, is then reduced, water being formed together with the protons ($4\ e^- + 4H^+ + O_2 \rightarrow 2H_2O$), so that the overall reaction is $2H_2 + O_2 \rightarrow 2H_2O$.

As already mentioned previously, the water obtained is supplied once again to the splitting process at the anode side of the PEM cell.

The second method can be carried out pursuant to the invention owing to the fact than an electrolyzer and a fuel cell are combined in one cell, preferably as a PEM cell. Pursuant to the invention, the step of producing the gaseous hydrogen by electrolysis and of passing this hydrogen on as a starting material for a fuel reaction is omitted here, only a polymer membrane being used as electrolyte. On the anode side, the water supplied is split catalytically into oxygen ions and hydrogen ions ($H_2O \rightarrow O^{2-} + 2H^+$). The hydrogen ions (protons) are passed through the polymer membrane to the cathode side of the cell and react there catalytically with the oxygen, supplied by the surrounding air, to form water according to the equation $4H^+ + O_2 + 4\ e^- \rightarrow 2H_2O$. The water, so formed, can be returned once again and supplied to the anode side of the cell.

At the anode side, the oxygen ions then form oxygen, emitting electrons according to the equation $2O^{2-} \rightarrow O_2 + 4\ e^-$. The gaseous oxygen can then be discharged from the cell and mixed appropriately with the air respired by the user.

In both variations of the inventive method, gaseous, pure oxygen is produced in bubble form on the anode side in the water supplied, then discharged and in one embodiment of the invention, passed into a water separator, in which the bubbles of pure oxygen can be separated from water and then discharged appropriately.

It has turned out that only about 8% of the total volume during the inhalation phase of a person can be converted in the lung and transferred to the circulating blood. The inventive device makes available an electronic control unit, which preferably is controlled by a microprocessor and is also referred to as a demand system, which makes only precisely this amount available at the start of the inhalation phase of the user, that is, this particular amount is mixed with the air respired by the user in the respiration intervals.

For this reason, an electrolyzer is already suitable as a unit with relatively small dimensions, relatively small amounts of water being made available as the starting material for producing oxygen.

The hydrogen, formed at the same time, can be discharged, for example, catalytically over a combustion tube as water vapor to the surroundings or, in a preferred embodiment, in which the electrolyzer is coupled with the fuel cell, converted together with air from the surroundings back into water in the fuel reaction coupled thereto.

Pursuant to the invention, either a direct mains connection or an exchangeable battery can be used as supplier for electrical energy for carrying out or maintaining the individual reactions.

In a particularly advantageous development of the invention, a further fuel cell, preferably a direct methanol fuel cell, serves as a supplier of power, the methanol optionally being made available by a cartridge system.

In a further advantageous development of the invention, the oxygen is collected in a storage system, from which it is then taken selectively by means of the electronic control unit and supplied to the user.

In one embodiment of the invention, the producing unit, the pressure storage system, the supply pipeline and the electronic control unit form a unit, which is constructed so that the unit as a whole is portable and can be carried by being strapped onto the patient.

The electrical energy, required for carrying out the production of oxygen, is made available by an electric source of energy, preferably by a connection to the mains. Pursuant to the invention, this source of electric energy can be stationary. It forms a so-called "docking unit", into which the mobile unit of the device can be inserted and to which it can be coupled, so that the oxygen-producing process can take place. In other words, the mobile unit can be used in its mobile stage, separated from the energy source, as long as there is oxygen in the storage system. When the pressurized storage system is empty, the mobile unit is connected once again with the source of electrical energy, so that it can be filled with pure oxygen. The size of the pressurized storage system determines the time period during which the mobile unit can be used.

The generating unit either has a separate inlet for the water that is required, through which it can be filled, for example, from a pressurized storage unit, or, in one embodiment of the invention, a connection, which is connected with a water-supplying pipeline, which is provided at the stationary "docking unit".

It becomes clear that, due to the use of an electrolyzer and a fuel cell, which are either separate from one another or combined in a single cell, which preferably is constructed as a PEM cell, a light and compact unit is formed, which operates extremely quietly because of the reaction taking place therein. Moreover, the electronically controlled selective acceptance of the oxygen produced enables the unit to be reduced in size extensively, since the whole of the inhalation volume of oxygen does not have to be produced, but only certain fraction thereof. The use of conventional water as a supplier of oxygen also simplifies the use of this device, so that it can be used without problems at home and, in an advantageous development of the invention, can also be configured as a mobile unit.

Further advantages and developments of the devices arise out of the dependent claims.

BRIEF DESCRIPTION OF THE DRAWINGS

In the following, the mode of functioning of the principle, on which the inventions is based, is to be explained in greater detail by examples shown in the attached drawings, in which.

DETAILED DESCRIPTION OF THE INVENTION

Figure 1:
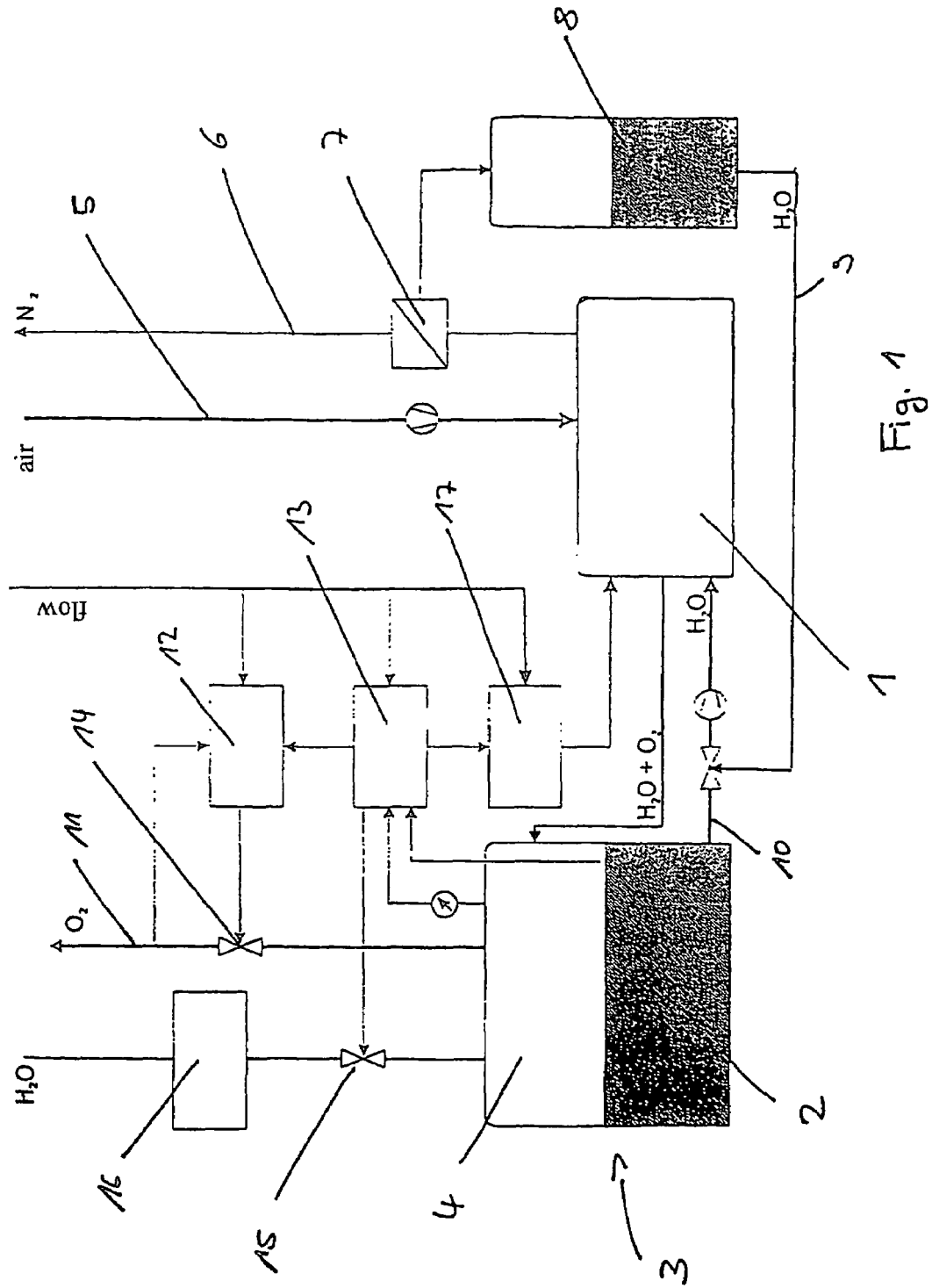
FIG. 1 shows a block circuit diagram showing the method and the device of the invention and FIG. 2 shows a diagrammatic representation of an inventive device as a mobile unit.

FIG. 1 shows a block circuit diagram of the inventive principle of generating oxygen with a generating unit 1. Depending on the embodiment, the generating unit 1 consists either of an electrolyzer, which is coupled with a fuel cell, or of a single PEM cell, which combines the functions of an electrolyzer and a fuel cell. The basic construction of such cells is generally known.

The generating unit 1 is supplied with water as starting material from a water storage system 2. The corresponding reactions of the electrolysis and of the fuel cell then take place in the generating unit 1.

Pure oxygen is formed as bubbles in the water present at the anode side of the generating unit 1. This water is discharged together with the oxygen and supplied to a water separator 3, in which the pure oxygen is separated from the water, so that the water separator 3 can function, on the one hand, as an oxygen storage system 4 and, on the other, as a water storage system 2.

At the cathode side of the generating unit 1, air from the surroundings is supplied over a pipeline 5, in order to make the conversion back into water possible. The resulting water, as well as the oxygen obtained, are discharged over a common pipeline 6, also over a water separator 7.

After it is collected in a water storage system 8, the water is added over a recycling pipeline 9 to the supplying pipeline 10 from the water storage system 2, so that a closed cycle is formed.

The pure oxygen form the oxygen storage system 4 is supplied over a feed pipeline 11 to the air respired by the patient.

An electronic control system 12, which is also referred to as a demand system and is controlled by a CPU 13, regulates the selective removal of pure oxygen over a valve 14.

The CPU 13, once again over a valve 15, controls the supplying of water from a water-replenishing system 16.

The CPU 13 or the demand system 12 can be connected with sensors, which determine the amount of the pure oxygen required, as a function of the inhalation of the user.

The whole system is supplied with electrical energy required for carrying out the control and the splitting and conversion processes, from an energy source, which is not shown and may be constructed as a battery, a mains connection or a further fuel cell, a current transformer 17 being used.

Figure 2:
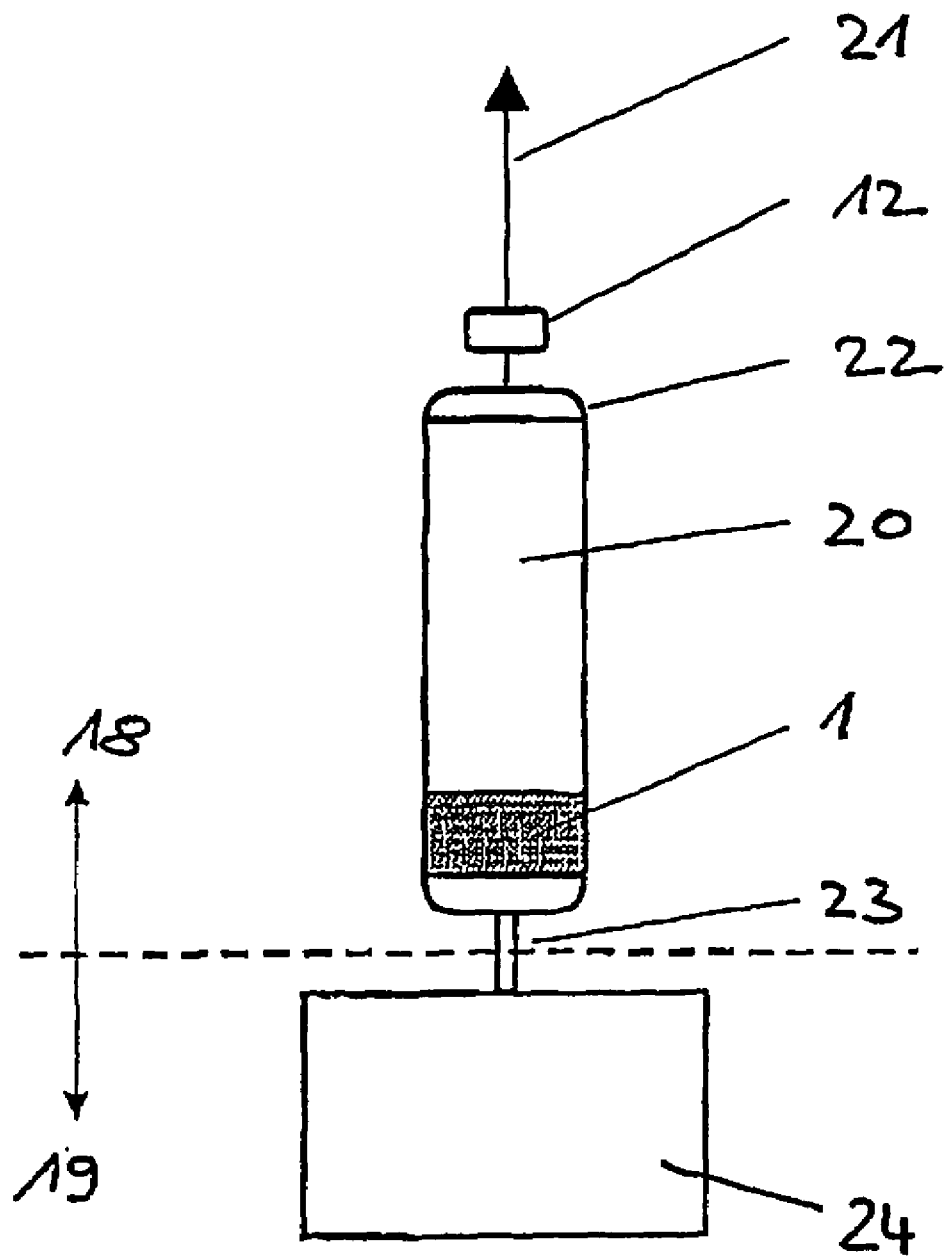

FIG. 2 diagrammatically shows an inventive device, which consists of mobile unit 18 and a stationary unit 19.

The mobile unit 18 consists of an oxygen-generating unit 1, a pressurized storage system 20, which is connected directly to the generating unit 1 and in which the pure oxygen, generated by electrolysis, is collected.

A pressure reducer 22 is provided between the pressurized storage system 20 and the pipeline 21 supplying the patient. The supplying pipeline 21 is coupled by known valve techniques with an electronic system 12, so that pure oxygen is taken from the pressurized storage system 20 at certain intervals only at particular times of the inhalation phase and supplied to the air respired by the patient and the concentration of oxygen in this air is increased selectively.

The generating unit 1 of the mobile unit 18 is connected over an electrical lead 21 with the electric mains part 24 of the stationary unit 19.

The invention of claimed is:

1. Method for increasing concentration of oxygen in respired air, comprising
   electrolyzing water into oxygen and hydrogen;
   mixing the oxygen from the electrolyzing step with respired air;
   reacting the hydrogen from the electrolyzing step by a fuel reaction with oxygen from ambient air to form water and produce electrical energy, wherein the step of electrolyzing and the step of reacting take place simultaneously and continuously to comprise a reaction cycle; and
   cycling at least a portion of the electrical energy produced by the reacting step for use in the electrolyzing step thereby reducing the amount of electrical energy required to be supplied by an external source for the electrolyzing step.

2. The method of claim 1, further comprising cycling at least a portion of the water produced by the fuel reaction to the electrolyzing.

3. The method of claim 1 or 2, comprising supplying electrical energy required for starting and/or maintaining the reaction cycle, from a source of electrical energy other than the electrical energy produced by the step of reacting.

4. The method of claim 1 or 2, wherein the electrical energy required for starting and/or maintaining the reaction cycle, is supplied exclusively from the reacting step or with a separate additional fuel reaction to which additional hydrogen that does not originate from the electrolysis is supplied for reaction with oxygen from ambient air.

5. The method of claim 4, comprising producing the hydrogen for the additional fuel reaction from methanol.

6. Method for increasing the concentration of oxygen in respired air, comprising
   splitting water by application of electrical energy and catalysis into hydrogen ions and oxygen ions,
   combining the oxygen ions from the splitting step to form oxygen $O_2$ and emit electrons;
   admixing the oxygen from the combining step with respired air; and
   reacting catalytically the hydrogen ions from the splitting step with the emitted electrons from the combining step and oxygen from ambient air to form water,
   wherein the splitting step, the combining step, the admixing step and the reacting step take place simultaneously and continuously to comprise a reaction cycle.

7. The method of claim 6, comprising cycling at least a portion of the water produced by the reaction of the hydrogen atoms with the oxygen from the ambient air and the electrons to the splitting step.

8. The method of claim 6 or 7, comprising supplying at least a portion of electrical energy required for commencing and/or maintaining the reaction cycle, from a source of electrical energy other than the electrical energy produced by the step of reacting.

9. The method of claim 6 or 7, comprising supplying at least a portion of electrical energy required for commencing and/or maintaining the reaction cycle, from a separate fuel reaction to which additional hydrogen that does not originate from the splitting step is supplied for reaction with oxygen from ambient air.

10. The method of claim 9, comprising producing the hydrogen for the separate fuel reaction from methanol.

11. Apparatus for increasing concentration of oxygen in respired air, comprising an oxygen generating unit, a source of electrical energy, a feed conduit from the generating unit to a user and an electronic control unit which controls mixing of the generated oxygen with air respired by the user.

12. The apparatus of claim 11 wherein the generating unit comprises an electrolyzer for splitting water into oxygen and hydrogen.

13. The apparatus of claim 11 or 12, wherein the source of electric energy comprises at least one of a battery and a alternating current electrical power supply connection.

14. The apparatus of claim 11 or 12, wherein the source of electrical energy comprises a separate fuel cell.

15. The apparatus of claim 14, wherein the fuel cell is a direct methanol fuel cell.

16. The apparatus of claim 15, comprising a disposable or reusable cartridge system for the methanol.

17. The apparatus of claim 14, further comprising a refillable or exchangeable fuel storage system connected to the separate fuel cell.

18. The apparatus of claim 11 or 12, further comprising, situated between the oxygen generating unit and the feed conduit, an integrated or removable oxygen storage system in which the oxygen generated by the generating unit, is collected and removal from which is controlled by the electronic control unit for mixing with the respired air.

19. The apparatus of claim 18, further comprising, connected to the electronic control unit, sensors for measuring oxygen required by the user.

20. The apparatus of claim 19, wherein all or respective portions of the apparatus are in stationary or mobile form.

21. The apparatus of claim 20, further comprising a source of electrical energy and wherein the generating unit, the oxygen storage system, the feed conduit and the electronic control unit comprise a mobile unit and the source of electrical energy comprises a stationary unit and the mobile and stationary units are adapted to be connected to one another for generating and storing oxygen.

22. The device of claim 21, wherein the stationary unit further comprises a connection for water.

23. The apparatus of claim 22, further comprising a pressure reducer provided between the oxygen storage system and the feed conduit, wherein the oxygen storage system is a pressurized storage system.

24. The apparatus of claim 21, wherein the oxygen storage system is a pressurized oxygen storage system.

25. The apparatus of claim 11 wherein the oxygen generating unit is comprised of an electrolyzer for splitting water into oxygen and hydrogen: and a fuel cell for reacting hydrogen with oxygen from ambient air to form water, the fuel cell and electrolyzer being coupled together for transfer of fluids and electrically in such a manner that at least a portion of electrical energy produced by the fuel cell is used to decrease energy required by the electrolyzer and at least a portion of the water produced by the fuel cell is cycled to the electrolyzer.

26. The apparatus of claim 25, wherein at least one of the electrolyzer and the fuel cell is constructed as a polymer electrolyte membrane cell.

27. The apparatus of claim 26, further comprising a refillable or exchangeable fuel storage device connected to the fuel cell.

28. The apparatus of claim 27, further comprising a fuel reformer connected to the fuel storage device.

29. The apparatus of claim 27, wherein the hydrogen storage device comprises a metal hydride.

30. The apparatus of claim 27, wherein the hydrogen storage device comprises a device for storing hydrogen under pressure.

31. The apparatus of claim 25, wherein the electrolyzer and the fuel cell are combined in a single cell.

32. The apparatus of claim 31, wherein the single cell is a polymer electrolyte membrane cell.

* * * * *